(12) United States Patent
Quinn et al.

(10) Patent No.: US 12,138,407 B1
(45) Date of Patent: Nov. 12, 2024

(54) SHORT LENGTH FLEXIBLE CATHETER WITH HOLLOW GUIDE WIRE

(71) Applicant: CraniUS LLC, Baltimore, MD (US)

(72) Inventors: Charlotte Quinn, Baltimore, MD (US); Jack Kent, Baltimore, MD (US)

(73) Assignee: CraniUS LLC, Baltimore, MD (US)

( * ) Notice: Subject to any disclaimer, the term of this patent is extended or adjusted under 35 U.S.C. 154(b) by 0 days.

(21) Appl. No.: 18/356,570

(22) Filed: Jul. 21, 2023

(51) Int. Cl.
*A61M 25/09* (2006.01)
*A61M 25/01* (2006.01)

(52) U.S. Cl.
CPC .... *A61M 25/0905* (2013.01); *A61M 25/0108* (2013.01); *A61M 25/0194* (2013.01); *A61M 2025/0197* (2013.01); *A61M 2210/0693* (2013.01)

(58) Field of Classification Search
CPC .. A61M 2210/0687; A61M 2210/0693; A61M 25/00; A61M 25/0662; A61M 25/09; A61M 25/0053; A61M 2025/09091; A61M 2005/2013; A61M 2205/581; A61M 5/2033; A61M 5/3157; A61M 5/31578; A61M 5/3204; A61M 5/20; A61M 5/31571; A61M 25/0905; A61M 25/0108; A61M 25/0194; A61M 2025/0197
See application file for complete search history.

(56) References Cited

U.S. PATENT DOCUMENTS

| | | | | |
|---|---|---|---|---|
| 5,318,576 A | * | 6/1994 | Plassche, Jr. | .. A61B 17/320725 606/159 |
| 6,030,369 A | * | 2/2000 | Engelson | .......... A61M 25/0045 604/525 |
| 2009/0198218 A1 | * | 8/2009 | Gill | ........................ A61M 25/02 604/524 |
| 2012/0296275 A1 | * | 11/2012 | Martin | .............. A61M 25/0662 604/103.05 |
| 2017/0106171 A1 | * | 4/2017 | Flores | .................. A61M 25/09 |

* cited by examiner

*Primary Examiner* — Brandy S Lee
(74) *Attorney, Agent, or Firm* — Maier & Maier, PLLC

(57) ABSTRACT

A short length flexible catheter with hollow guide wire and flushing port for convection enhanced delivery may be provided. The short length CED catheter may include a catheter body made of silicone or plastic. The short length catheter may further include an attachment port connected to a first end of the flexible, hollow guide wire contained within the catheter body. The hollow catheter guide wire may extend beyond the catheter body on one end for both enhanced tunneling and simultaneous use of flushing.

9 Claims, 2 Drawing Sheets

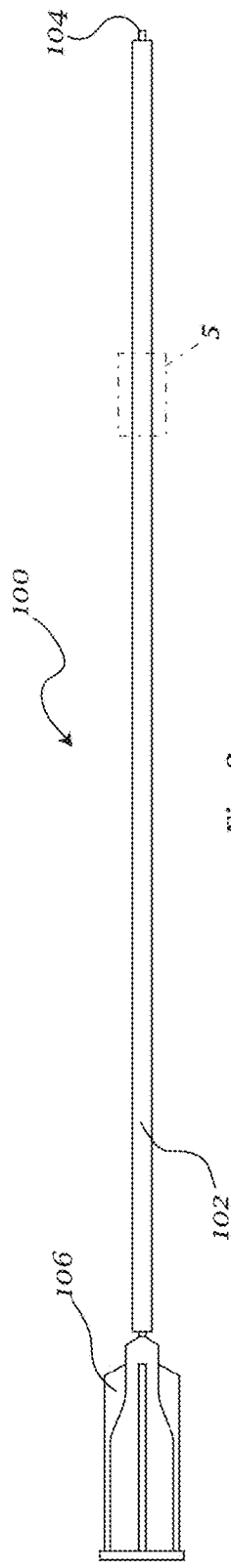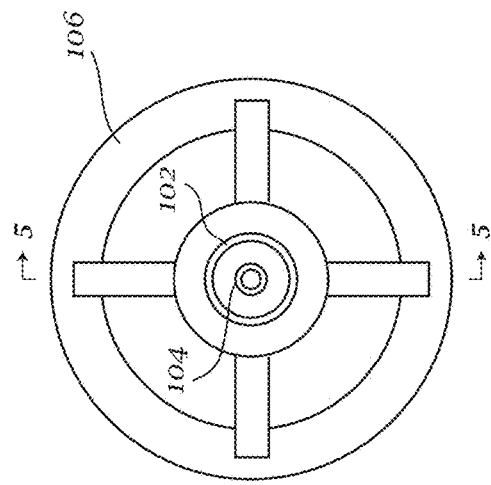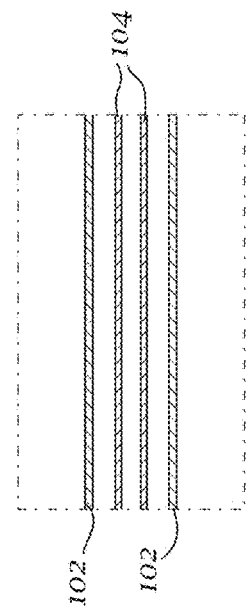

SHORT LENGTH FLEXIBLE CATHETER WITH HOLLOW GUIDE WIRE

BACKGROUND

The creation and safe use of a medicine delivery device is a longstanding goal of all healthcare providers wishing to treat and care for patients suffering from chronic disease. More specifically, successful delivery devices are able to reduce required and/or repetitive surgeries, improve and ensure patient compliance, target specific areas of the body thereby increasing drug safety and efficacy (in turn reducing systemic toxicity side effects), and ease the process of providing lifesaving medicine for which both oral and systemic delivery routes are ineffective due to pre-existing tissue barriers (i.e. blood-brain barrier); such as when, for example, surgery is deemed suboptimal and/or less effective like with chronic disease management.

For instance, some brain pathology cannot be simply "cut out" by a surgeon for symptom eradication, and hence, direct brain medicine delivery may be necessary to overcome this barrier and to best control chronic diseases. In some cases, these skull-embedded devices need to precisely control and monitor exactly how much of a medicine is being introduced into the specific body part and/or organ on an hourly, daily, weekly, or otherwise regular basis. As a result, there is a serious concern and critical need for ensuring that the catheter(s) used for direct medicine delivery has certain properties which optimize both safety and efficacy. Current catheters designed for direct medicine, pump-assisted, convection-enhanced delivery include solid (not hollow) guidewires or stylets, as well very long lengths (significantly greater than 18 inches) given that all current designs for connection-enhanced delivery (CED) utilize either: 1) an implanted, metal device placed within the subcutaneous pocket of a human's back/abdomen, or 2) an extra-anatomical device attached the wall or IV pole with the catheter extending well outside the anatomical limits of the human skull/scalp. Both scenarios require a significant amount of catheter length. Similarly, length has a scientific relation to flow. According to Poiseuille's scientific law, the flow rate through a catheter is inversely proportional to the length. Thus, longer lengths of catheter may result in lower output flow rates, which may be disadvantageous given that convection-enhanced delivery (CED) requires a "jet-like gradient" at the distal opening of each catheter.

Currently, many long-length catheters for delivering medicine from implantable devices in the head or near the brain are not only excessively long, but they are also rigid in form. The catheter doesn't move, bend and/or get kinked thereby, however this inhibits the neurosurgeon from placing the catheters in a non-linear position within the white matter of the brain, and thus has the potential to inhibit optimal medicine flow through the catheter. This rigid characteristic may be further undesirable in instances where a skull-embedded device capable of chronic CED is designed and engineered to sit either directly above and/or off-center from the underlying brain just a few centimeters away. This is because the catheter(s) may need to exit the device at a curve which would be impossible with a rigid-type catheter. Secondly, rigid catheters have a higher incidence of backflow during CED, which may be a major impediment to the operation of the pump-assisted CED device.

Many current brain catheters have issues that result in blockage of the catheter. One reason this may happen is when blood particles and/or platelets adhere and stick within the lumen of the catheter (e.g. during the time of insertion and brain tunneling). Additionally, there are brain particles which may obstruct the lumen and inhibit effective CED at the time of pump activation. The catheters, being typically placed with a solid stylet or guidewire, may also house air bubbles within once the stylet or guidewire is removed. By a sequence of events, the risk of air being pushed into brain tissue is substantial and can be life-threatening. Similarly, trapped particles (blood clots or human tissue particles), can inhibit optimized flow of medicine to the point of near-complete or complete obstruction. It is difficult to reliably and safely flush current microcatheters; current practices generally include using micro irrigators which do a suboptimal job reaching the distal portion of the typical long length catheter, and fail to have any type of effective connection (i.e. a male-to-female relation between the syringe full of sterile saline and the CED catheter in place within the brain).

SUMMARY

In some embodiments, a flexible catheter with hollow guide wire and flushing port for convection enhanced delivery may be provided. The catheter may include a catheter body made of silicone or plastic. The catheter may further include a flexible, hollow guide wire contained within the catheter body for enhanced tunneling and an attachment port connected to a first end of the guide wire. The catheter guide wire may extend beyond the catheter body on one end. The catheter may have a shorter length to optimize flow and minimize resistance in an effort to achieve a pressure gradient critical for CED success.

BRIEF DESCRIPTION OF THE FIGURES

Advantages of embodiments will be apparent from the following detailed description of the embodiments. The following detailed description should be considered in conjunction with the accompanying figures in which:

FIG. 2 shows an exemplary top view of the short-length flexible catheter design.

FIG. 3 shows an exemplary rear view of the short-length flexible catheter design.

FIG. 4 shows an exemplary front view of the short-length flexible catheter design.

FIG. 5 shows a cross section of the exemplary short-length flexible catheter design.

DETAILED DESCRIPTION

Figure 1:
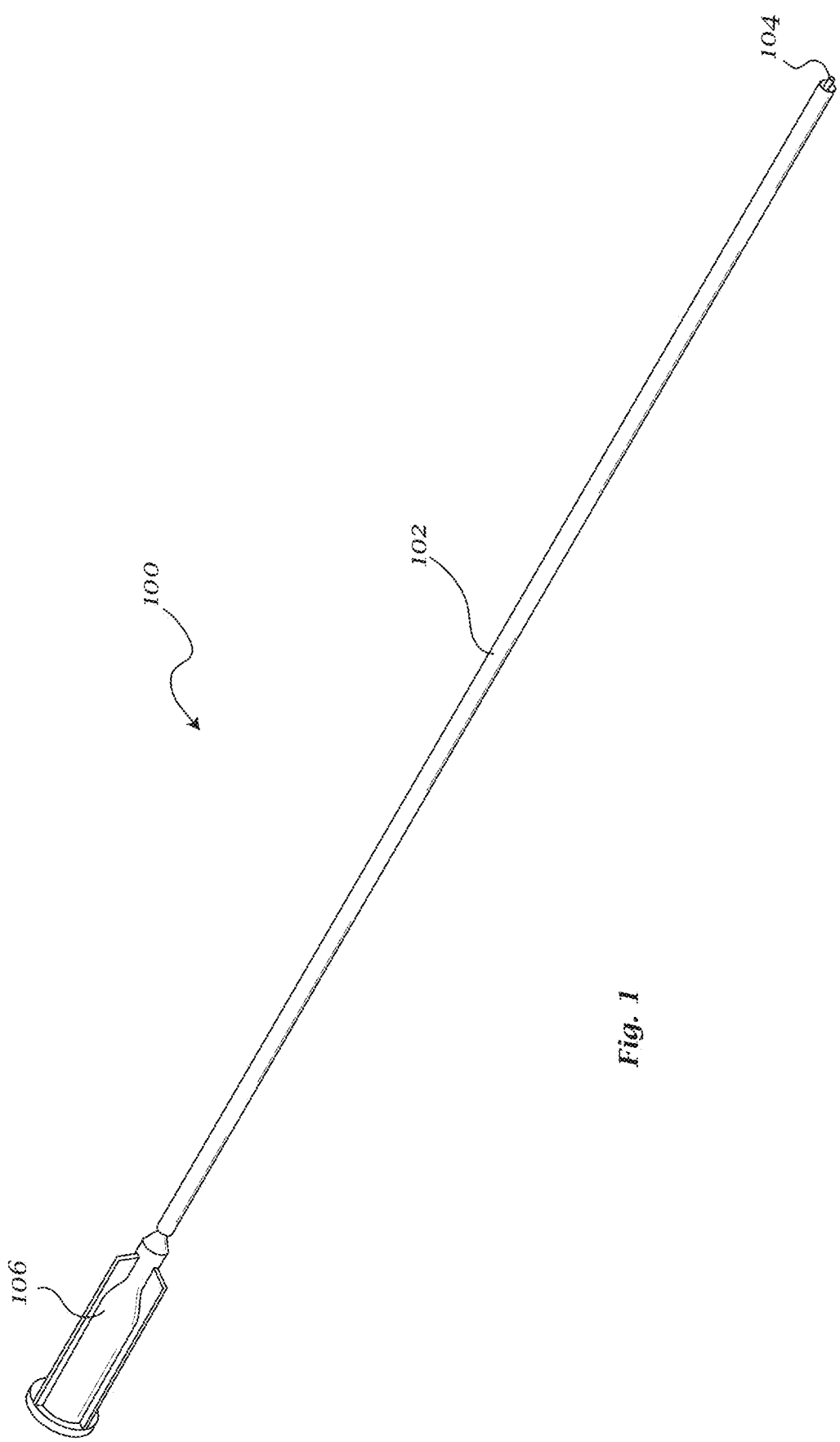
FIG. 1 shows an exemplary short-length flexible catheter design.

Aspects of the invention are disclosed in the following description and related drawings directed to specific embodiments of the invention. Alternate embodiments may be devised without departing from the spirit or the scope of the invention. Additionally, well-known elements of embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

As used herein MRI-safe may be understood to mean a device that when used in the MRI environment presents no additional risk to the patient or other individual, but it may affect the quality of the diagnostic information.

As used herein MRI-compatible may be understood to mean a device that is MRI safe when used in the MRI environment, and neither significantly affects the quality of the diagnostic information nor has its operations affected by the MRI system.

In one or more embodiments, a short-length flexible catheter with hollow guide wire and flushing port for convection enhanced delivery may be provided.

The following sections generally describe an embodiment of the short-length flexible catheter with reference to exemplary FIGS. 1-5, where exemplary FIG. 1 shows a flexible catheter design 100, exemplary FIG. 2 shows a top view 200 of the flexible catheter design, exemplary FIG. 3 shows a rear view 300 of the flexible catheter design, exemplary FIG. 4 shows a front view 400 of the flexible catheter design and exemplary FIG. 5 shows a cross section 500 of the flexible catheter design.

The short-length exemplary catheter 100 may have a catheter body 102, which may be a tube made of, for example, silicone or plastic. In another embodiment, the catheter body 102 may be made from biocompatible silicone and/or alloplastic. It may be understood that the catheter body may be MRI-safe and MRI compatible. In an embodiment, the catheter body 102 may be flexible, for example by virtue of material composition and dimensions. In another embodiment, the catheter body 102 may be, for example, silicone or plastic having a small outer diameter, such as 1 to 5 mm, and small wall thickness, such as 0.3 to 1 mm, which may allow for tight bend radii of the catheter without kinking. The catheter body 102 may be a precise length applicable for chronic, convection enhanced delivery. The catheter body length may be chosen to best accommodate the distance between the intended delivery site (i.e. brain) and the drug delivery mechanism (i.e. housed within the skull space in close proximity). For example, in an embodiment involving a catheter(s) connecting to a skull-embedded device, the catheter may be 1-4 inches long.

The short-length catheter 100 may further include a hollow guide wire 104, which may thread through the catheter body 102. In an embodiment, the hollow guide wire 104 may be flexible, for example owing to material composition and dimensions. For example, the hollow guide wire may be composed of metal or plastic and have a small outer diameter and small wall thickness, which may provide just enough flexibility to facilitate guidance and advancement of the more flexible catheter body. In an embodiment, a first end of the hollow guide wire 104 may extend just beyond the end of the catheter body 102. In an embodiment, the guide wire 104 may have a smaller outer diameter than the catheter body 102 and be made of a slightly less flexible material, for example where the guide wire 104 is metal and the catheter body 102 is silicone, and therefore may be more easily tunneled into the brain tissue in preparation of receiving chronic medicine delivery. Therefore, the guide wire 104 may extend from one end of the catheter body enough to ease catheter insertion. For example, in an exemplary application, the hollow guide wire 104 may extend beyond the catheter body 102 by 1-2 millimeters. In some embodiments, the hollow guide wire 104 may allow for integration with other medical devices including, for example, navigation platforms. Because the hollow guidewire described here has metallic properties, it accompanies an advantage of showing up on stereotactic navigation, which significantly helps with precise brain catheter positioning and minimizing injury to nearby structures (i.e. ventricle, sagittal sinus blood vessel). A second end of the hollow guide wire 104 may interface with a hub 106 or attachment port. In some embodiments, the hub 106 may interface with an optical or electromagnetic guidance system. In some embodiments, the hub 106 may interface with a syringe, for example a "Luer lock" or "slip tip" syringe, and may allow for the administration of fluids, for example medication or saline, through the short-length catheter 100. In some embodiments, the hub 106 may be configured such that fluids may be flushed through the catheter 100 in order to prevent air emboli from forming and/or in order to prevent or remove clogging particles. In some embodiments, the short length catheter body 102 may have a unique design configuration to allow for high precision and accuracy in flushing within a short length design. Additionally, it may be understood that the shorter length means that there is less internal room and therefore less potential for trapped air bubbles (ie. risk of life-threatening air emboli). Notably, a shorter length also improves catheter flow efficiency and evidence of "convection", which has been hard for some long length catheters to achieve reliably.

In an embodiment, the exemplary short-length catheter 100 may be utilized in conjunction with a skull-embedded implant. In the exemplary embodiment the internal guide wire 104 may be exactly 1-2 millimeters longer than the catheter body 102 and may be positioned to tunnel through a brain parenchyma in order to attach to the brain implant. In some embodiments, by limiting the excess length of the guide wire 104 to 2 mms it may be understood that there may be a decrease in the risk of undesirable guide wire bending-given that there is no outside support provided by the catheter 100. In other embodiments, it may be understood that by having at least 1 mm of excess guide wire 104, there may be sufficient sharpness to the catheter to allow for blunt tunneling through the brain. In an embodiment, the catheter 100 may also be made of a radiopaque material and guided using, for example, stereotactic guidance. Stereotactics may be useful in embodiments where the aim is to land the distal end well within the white matter of the brain (which is where chronic neurological disease resides) and to avoid inadvertently injuring internal brain structures like blood vessels and/or ventricle; which can have devastating consequences.

It may be understood that CED requires a "jet-like gradient" to be present at the distal end of the catheter, which may forcefully push the medicine through the interstitial space. However it may be understood that if the force is too high, the brain may suffer traumatic injury, and that if the pressure is too low, the gradient may be ineffective in driving convection and that the fluid may either back up inside the catheter, or backtrack along the catheter circumference, for example within the tunnel of the brain created during catheter placement; given that these are both the paths of least resistance). Hence, a shorter length catheter, as in the embodiments, provides the neurosurgeon an enhanced length more likely to achieve a "jet-like" gradient critical for CED success (i.e. Poiseuille's scientific law) which may ensure CED success.

In an embodiment, insertion of the catheter 100 and a medical implant may involve constant flushing of saline through the hollow guide wire, which may be ex-vivo or on the operating table before placement and/or in-vivo which may be following placement and before connection to the implant. It may be understood that the length of the catheter may allow for increased reliability and safety in delivering medicine or other fluid from the medical implant. It may be further understood that after implantation the length of the catheter 100 may allow for reduced contact between the time the medicinal drugs exit the skull embedded device and enter the desired area, for example the white matter of the brain.

The foregoing description and accompanying figures illustrate the principles, embodiments and modes of operation. However, the scope should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A catheter comprising:
    a catheter body made of silicone or plastic the catheter body being in fluid communication with a therapeutic agent;
    a hollow flexible guide wire comprised of at least an MRI-safe and MRI-compatible metal, contained within the catheter body, wherein the flexible guide wire extends beyond a second end of the catheter body;
    an attachment port connected to a first end of the flexible guide wire; and
    the attachment port is configured to interface with a slip tip and/or Luer lock syringe, and allows for the flushing of fluids through the catheter body via the hollow guide wire.

2. The catheter of claim 1, wherein the catheter is MRI-safe and MRI-compatible.

3. The catheter of claim 2, wherein a second end of the catheter body is configured to attach to an implantable medical device embedded within a skull.

4. The catheter of claim 1, wherein the catheter body is formed from biocompatible silicone and/or an alloplastic material.

5. The catheter of claim 3, wherein the opening of the second end is configured to accept the placement of a flexible guide wire within the catheter body to better assist with safe and effective tunneling into the brain parenchyma.

6. The catheter of claim 1, wherein the saline flushed liquid is held within the catheter body to prevent any risk of air emboli into the brain during or after surgical placement.

7. The catheter of claim 1, wherein the catheter body is 1 to 4 inches long.

8. The catheter of claim 7, wherein the internal flexible guide wire within the catheter is hollow for effective flushing and 1-2 millimeters longer than the catheter body.

9. The catheter of claim 7, wherein the catheter is radiopaque and designed to be placed with stereotactic guidance by utilizing the flexible guide wire.

* * * * *